United States Statutory Invention Registration [19]

[11] Reg. Number: H686

Mullins [43] Published: Oct. 3, 1989

[54] ELECTRO-OPTICAL LIGHT MODULATOR FOR PROTECTION OF OPTICAL SYSTEMS AGAINST PULSED LASERS

[75] Inventor: William D. Mullins, Huntsville, Ala.

[73] Assignee: The United States of America as represented by the Secretary of the Army, Washington, D.C.

[21] Appl. No.: 268,313

[22] Filed: Nov. 7, 1988

[51] Int. Cl.[4] ..... G02F 1/13; G02B 5/30

[52] U.S. Cl. ..... 350/352; 350/332; 350/374; 350/355

*Primary Examiner*—Thomas H. Tarcza
*Assistant Examiner*—Linda J. Wallace
*Attorney, Agent, or Firm*—Freddie M. Bush; James T. Deaton; Hay Kyung Chang

[57] ABSTRACT

An electro-optic shutter containing liquid crystal material is used to protect optical systems from pulsed laser radiation. The shutter provides the protection by being positioned between the optical system and the pulsed laser radiation and by rapidly alternating between clear and dark states. The alternation occurs in response to the absence or presence of an electric field in the shutter. When the electric field is absent, the shutter becomes clear and admits light and thus visual information whereas presence of the electric field causes the shutter to become dark and prevent the pulsed laser radiation from reaching the optical system. For protection of a binocular system such as the human eyes, in addition to the alternation of clear and dark states of each shutter, the clear-dark cycles of the shutters are staggered to assure that at any given moment at least one optical system is protected.

14 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ELECTRO-OPTICAL LIGHT MODULATOR FOR PROTECTION OF OPTICAL SYSTEMS AGAINST PULSED LASERS

DEDICATORY CLAUSE

The invention described herein may be manufactured, used, and licensed by or for the Government for governmental purposes without the payment to me of any royalties thereon.

BACKGROUND OF THE INVENTION

The ideal laser countermeasure system would protect optical sensor systems against all laser pulses with no degradation to sensor resolution. However, all laser protection schemes involve some tradeoff between the level of protection offered and the degradation in the performance of the optical system. The design of optical protection systems and devices is an exploration of these tradeoffs with the desired result of a system or a device which provides the most protection possible while retaining the highest degree of sensitivity possible to visual information. The simplest countermeasure is a neutral density filter which attenuates all light transmitted through it. A typical filter of optical density 1 blocks 90% of all laser light but at the cost of blocking 90% of the visual information available. In the case of the human eye, this reduction in the amount of information-containing transmitted light is somewhat offset by the increase in the diameter of the iris. A more sophisticated approach is the colored filter which uses wave length-selective absorbing filters or interference filters to attenuate threat laser light at specific wavelengths. But wavelength-selective absorbing filters have the disadvantage of blocking large bands of the visual spectrum for any particular threat wavelength, thereby limiting visual information transmission. Interference filters have narrower stop bands but are sensitive to the angle of the incoming light and susceptible to damage by high humidity. Neither the wavelength-selective absorbing filter nor the interference filter offers protection against the laser light which is within the passband of the filter.

SUMMARY OF THE INVENTION

An electro-optic shutter containing liquid crystal material which alternates between clear and dark states in response to the absence or presence of an electric field, respectively. Such a shutter is positioned between the optical system to be protected and the oncoming threat laser light. When the shutter is in the clear state, the transmission is high to maintain the visual throughput high and when the shutter is in the dark state, the transmission is low to provide substantial protection to the optical system. The shutter alternates between clear and dark states fast enough for the optical system being protected to perceive the scene as continuous. For a binocular system such as the human eyes, two electro-optic shutters may be used, one for each eye. In addition to each shutter alternating between clear and dark states, the clear-dark cycles of the two shutters are staggered, so that at any given moment, at least one optical system, or one eye in the case of humans, is protected from threat radiation.

DESCRIPTION OF THE PREFERRED EMBODIMENT

Figure 1A:
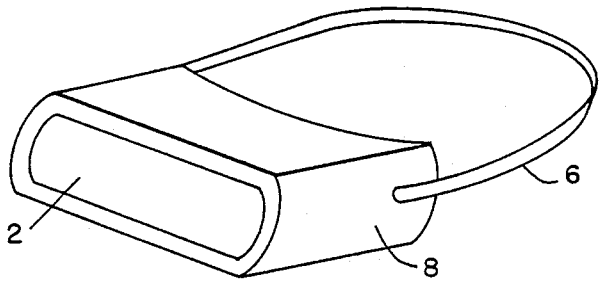
FIGS. 1A and 1B are exemplary protective electro-optic shutter devices for monocular and binocular systems, respectively.
Figure 1B:
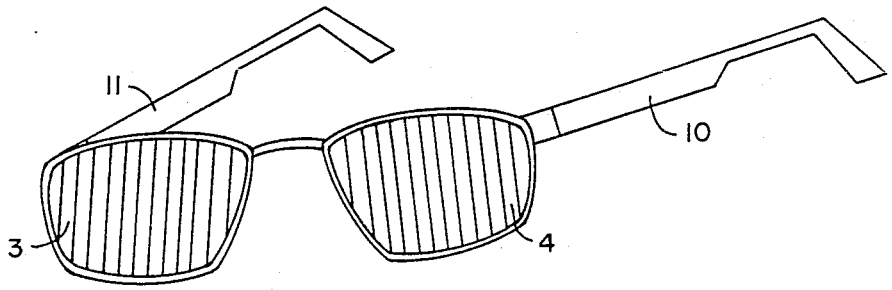

Referring now to the drawings wherein like numbers refer to like parts, FIGS. 1A and 1B depict typical shapes of monocular and binocular embodiments, respectively, of the invention. Electro-optic shutters 2,3, and 4, each is positioned between the optical system to be protected and the oncoming threat laser beam. Housing 8 of FIG. 1A and earpieces 10 and 11 of FIG. 1B contain the circuits which, by applying electric field at set time intervals to the shutters, control the alternation of the clear and dark states of each shutter. In a binocular shutter device, the housing also contains circuitry to control staggering of the clear-dark cycles of the shutters, so that the two shutters do not become clear simultaneously. This affords a binocular system, such as a pair of human eyes, an added degree of protection since at any given moment, at least one eye is protected from laser pulses. In FIG. 1A, strap 6 is slipped over the optical system to be protected and holds the electro-optic shutter in place. In FIG. 1B, the earpieces 10 and 11, in addition to housing the control circuitry, are perched over the ears to hold the shutters securely before the eyes.

Figure 2:
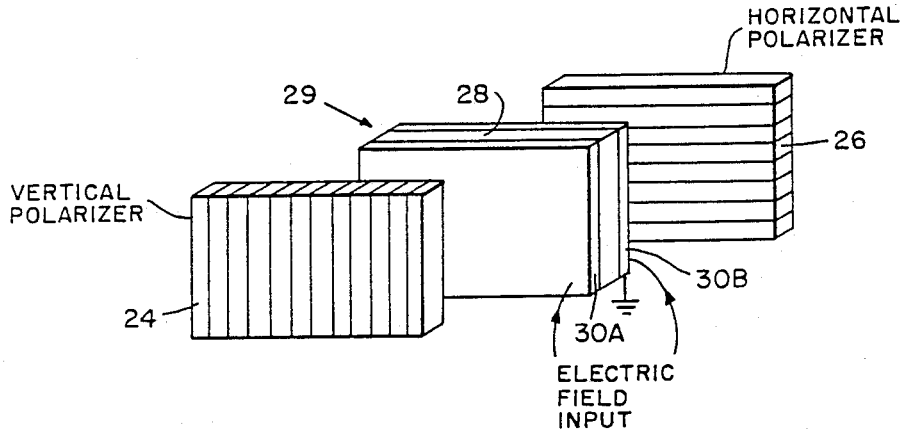
FIG. 2 schematically illustrates structure of an electro-optic shutter.

As can be seen in FIG. 2, shutters 2, 3 and 4 are each made of two light polarizers 24 and 26 and a liquid crystal layer 29 located therebetween. The plane of polarization of one of the polarizers is at 90 degrees to that of the other polarizer. Liquid crystal layer 29 in the middle is further made up of panels 30A and 30B of transparent electrically conductive material and a liquid crystal material 28 sandwiched between them. Panels 30A and 30B are required to be transparent to admit light and to be electrically conductive to respond to application of electric field by the control circuits. The liquid crystal layer may also be made of a porous block or a matrix of transparent electrically conductive material and droplets of liquid crystal material filling the pores or distributed throughout the matrix, respectively. Whatever the particular structure of the liquid crystal layer is the layer is selectively between 5 $\mu$m and 1 mm to provide a requisite thickness to cause polarization rotation by 90 degrees of radiation passing through it, when electric field is absent.

Figure 3:
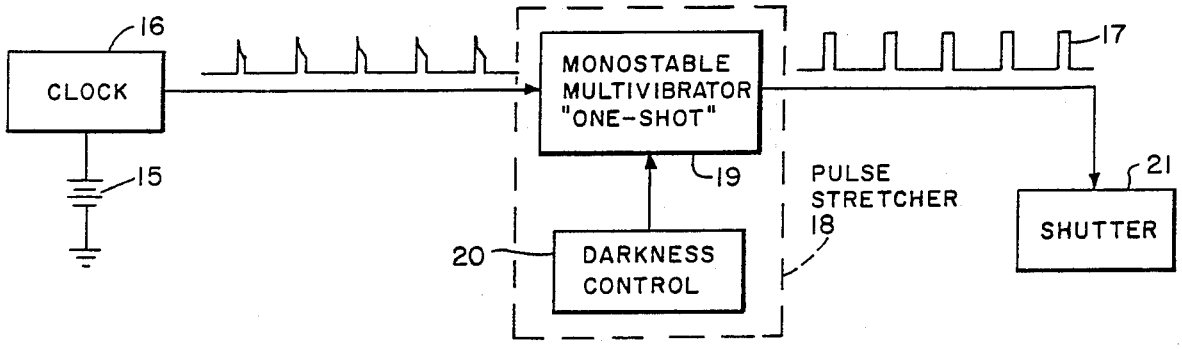
FIG. 3 illustrates a block diagram of a circuit to control the alternation of clear and dark states of a shutter to protect a monocular system.
Figure 4:
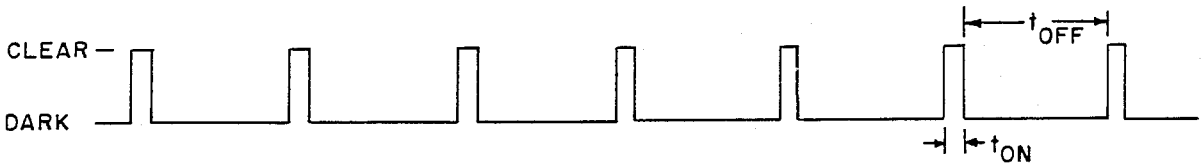
FIG. 4 is a graphic illustration of alternation between clear and dark states of a monocular electro-optic shutter device.
Figure 5:
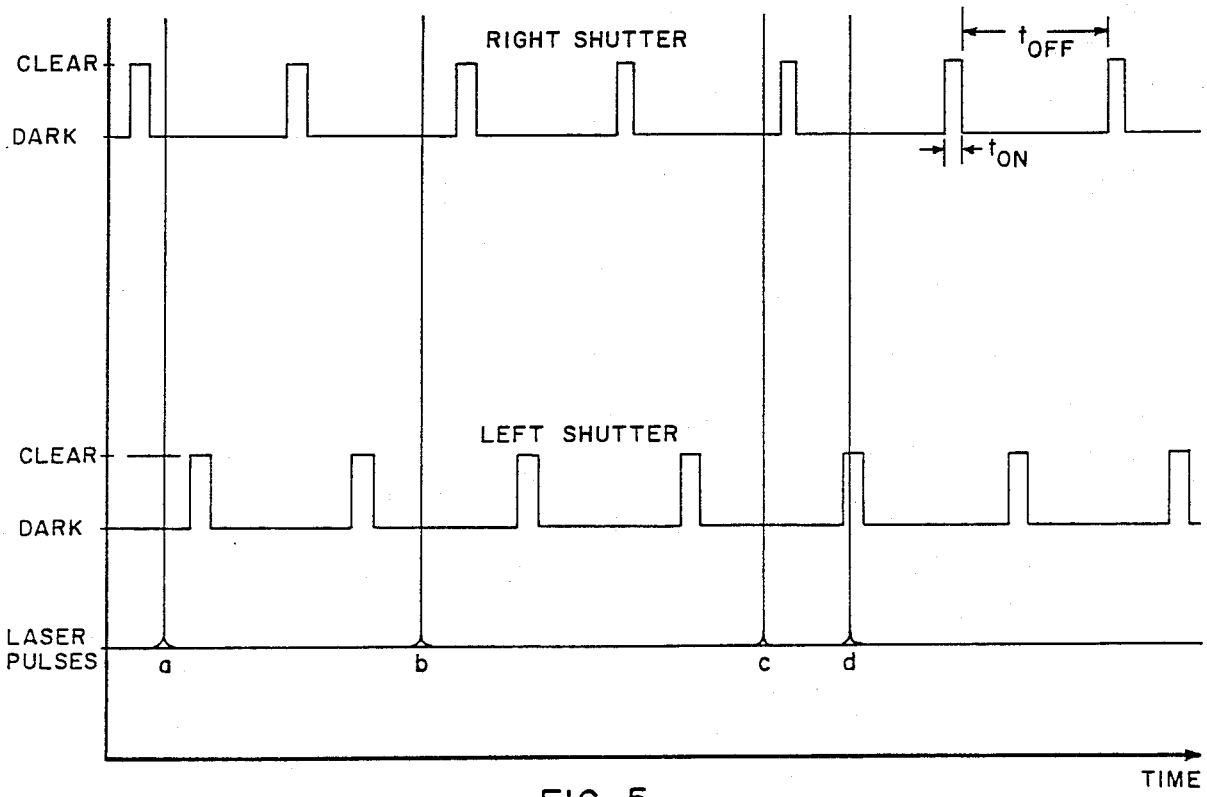
FIG. 5 is a graphic illustration of alternation of clear and dark states of the two shutters of a binocular electro-optic device.
Figure 6:
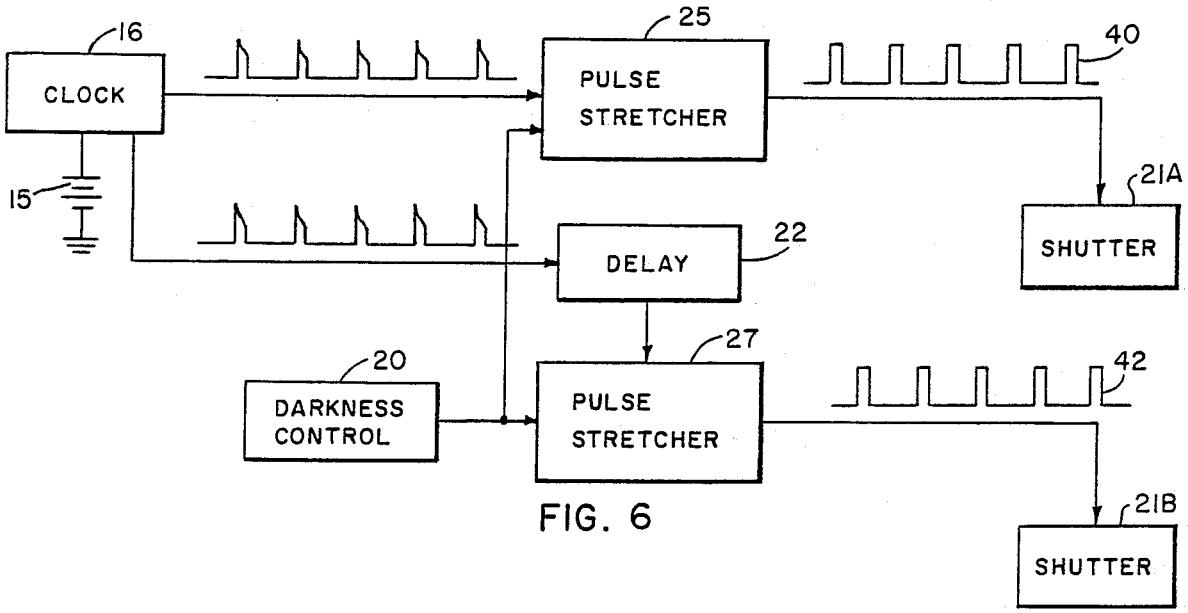
FIG. 6 illustrates a circuit including a delay circuit for shutters to protect a binocular system.

The circuit to control the monocular electro-optic shutter device is illustrated in FIG. 3. A power source 15 such as a battery drives a clock 16 which generates pulses at a preset frequency selectively between 30 Hz and 100 Hz. These pulses are fed into a pulse stretcher 18 comprised of a monostable multivibrator 19 and a darkness control mechanism 20. The pulses are then stretched into the series of square pulses 17 as illustrated. The stretched square pulses 17 are fed into the shutter containing the liquid crystal layer to cause the shutter to alternate between the clear and dark states. The series of square pulses 17 is shown in an enlarged mode in FIG. 4. When electric field from pulses 17 is applied across panels 30A and 30B, the shutter becomes dark and blocks radiation from its path to the optical system. As can be seen in FIG. 4, the shutter is in the dark state most of the time, so that for any particular laser pulse which may be incident on the optical system, the probability of transmission of that pulse is low and substantial protection is provided to the optical system. In a binocular device, as illustrated in FIG. 5, the clear-dark cycles are staggered between the two shutters so that even when a laser pulse such as d arrives at a time when one shutter is clear, one eye is protected since the other shutter shielding this eye is in a dark state blocking the laser pulse transmission. The circuitry for a binocular device with staggering is shown in FIG. 6 where delay circuit 22 delays the entrance of clock-produced pulses into pulse stretcher 27 so that one series of stretched square pulses 40 reach shutter 21A before the other series of stretched square pulses 42 reach 21B. Pulse stretcher 25 functions in the same way as pulse stretcher 18 in FIG. 3. Such alternation in the square pulses results in staggering of clear-dark cycles in the two shutters.

Figure 7A:
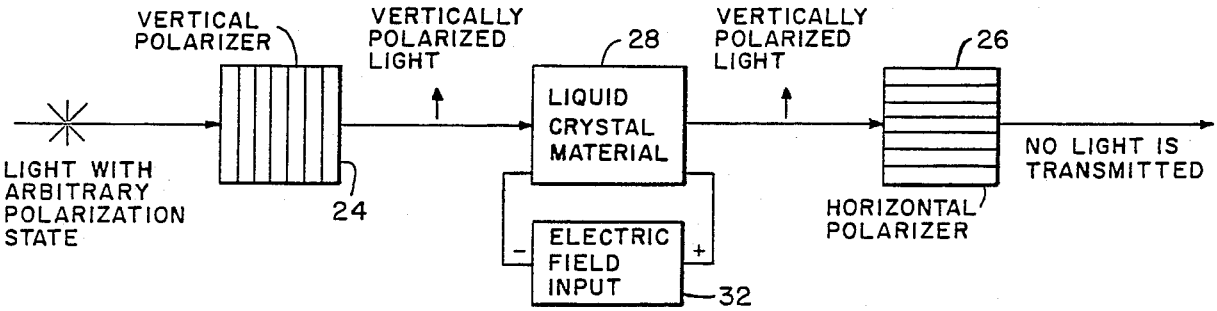
FIG. 7A illustrates the operation of the shutter during a dark state.
Figure 7B:
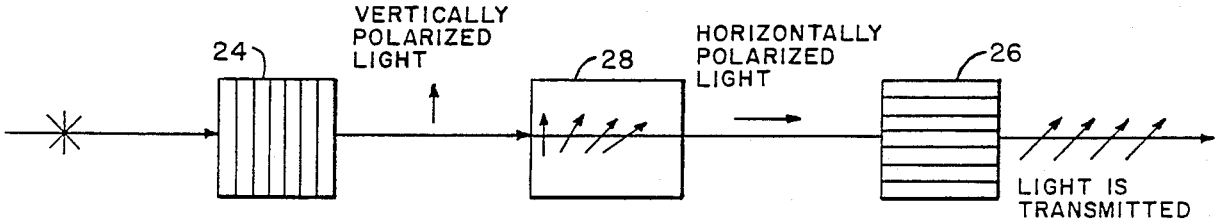
FIG. 7B illustrates the operation of the shutter during a clear state.

FIG. 7A shows how the shutter remains dark in the presence of electric field. For purposes of explanation, it is assumed that light travels from left to right and that polarizer 24 is a vertical polarizer whereas polarizer 26 is a horizontal polarizer. However, the position of the polarizers may be reversed as long as the plane of polarization of one polarizer is 90 degrees from that of the other polarizer. Light in a random polarization state enters the vertical polarizer which lets through only the vertically polarized portion of the light. This vertically polarized light portion next enters the liquid crystal layer 28. When electric field is present, the molecules of the liquid crystal material are horizontally aligned and have no effect on the plane of polarization of incident light, i.e. the molecules cause no polarization rotation to the light passing through. Therefore, the vertically polarized light portion passes through the liquid crystal layer with no change wrought on it. Then the light comes to the horizontal polarizer. Since the vertically polarized light portion has no horizontal component, no light passes through the horizontal polarizer and thus the shutter stays dark. In FIG. 7B, the electric field is absent from liquid crystal layer 28. In the absence of the electric field, the molecules of the liquid crystal material are in a random state and some have no effect on the incident light while others rotate the plane of polarization of the light so that the light leaving the liquid crystal layer is something other than completely vertically polarized light, i.e. the light leaving the liquid crystal layer has a horizontal component. This horizontal component passes through the horizontal polarizer and thus the shutter becomes clear.

Although a particular embodiment and form of this invention has been illustrated, it is apparent that various modifications and embodiments of the invention may be made by those skilled in the art without departing from the scope and spirit of the foregoing disclosure. Accordingly, the scope of the invention should be limited only by the claims appended hereto.

I claim:

1. A device for protecting optical systems from pulsed laser radiation, comprising:

an electro-optic shutter for alternating between clear state and dark state to respectively admit or inhibit radiation, a shutter control circuit coupled to drive said shutter to cause said shutter to alternate between the clear and dark states, a housing for containing said control circuit and means for mounting said shutter on an optical system such that said electro-optic shutter is disposed between the optical system to be protected and impinging radiation.

2. A device as set forth in claim 1 wherein said electro-optic shutter comprises a liquid crystal layer sandwiched between first and second polarizers, said first and second polarizers having their planes of polarization rotated 90 degrees relative to each other.

3. A device as set forth in claim 2 wherein said liquid crystal layer, when an electric field is absent therefrom, causes polarization rotation of a portion of said radiation by 90 degrees.

4. A device as set forth in claim 3 wherein said liquid crystal layer further comprises first and second panels of transparent electrically conductive material and liquid crystal material uniformly sandwiched between said panels.

5. A device as set forth in claim 4 wherein said liquid crystal layer for providing 90 degrees of polarization rotation is between 5 $\mu$m and 1 mm thick.

6. A device as set forth in claim 5 wherein said shutter control circuit comprises a clock for producing pulses at a set regular frequency, a pulse stretcher coupled between said clock and said shutter for stretching said pulses to control duration of said clear and dark states of said shutter and power source means coupled for driving said clock and said pulse stretcher.

7. A device as set forth in claim 6 wherein said set regular frequency is selectively between 30 Hz and 100 Hz.

8. A device for protecting optical systems from pulsed laser radiation, comprising:

electro-optic shutters for protecting first and second optical systems, said first and second shutters each adapted for alternating between clear and dark states to respectively admit or inhibit radiation, shutter control circuit means coupled to drive said shutters for causing said clear and dark states of said first shutter to be noncoincident with clear and dark states of said second shutter, a housing for housing said control circuit means and means for mounting said device on an optical system such that said first electro-optic shutter is disposed between said first optical system to be protected and impinging radiation, and said second electro-optic shutter is disposed between said second optical system to be protected and impinging radiation.

9. A device as set forth in claim 8 wherein said shutter control circuit comprises a clock for producing pulses at a set regular frequency, a first pulse stretcher coupled between said first electro-optic shutter and said clock, a delay circuit, a second pulse stretcher coupled between said second electro-optic shutter and said delay circuit, said delay circuit being further coupled to said clock for delaying said pulse output, said pulse output following an electronic path to said second pulse stretcher to produce non-simultaneous alternation of clear and dark states between said first and second electro-optic shutters.

10. A device as set forth in claim 9 wherein said first and second electro-optic shutters each comprises a liquid crystal layer sandwiched between a first polarizer and a second polarizer, said first and second polarizers having their planes of polarization rotated 90 degrees relative to each other.

11. A device as set forth in claim 10 wherein said liquid crystal layer, when an electric field is absent therefrom causes polarization rotation of a portion of said radiation by 90 degrees.

12. A device as set forth in claim 11 wherein said liquid crystal layer further comprises first and second panels of transparent electrically conductive material and liquid crystal material uniformly sandwiched between said panels.

13. A device as set forth in claim 12 wherein said set regular frequency is selectively between 30 Hz and 100 Hz.

14. A device as set forth in claim 13 wherein said liquid crystal layer for providing 90 degrees of polarization rotation is between 5 $\mu$m and 1 mm thick.

* * * * *